United States Patent [19]
Debono et al.

[11] Patent Number: 6,111,067
[45] Date of Patent: Aug. 29, 2000

[54] A-82846-TYPE GLYCOPEPTIDE ANTIBIOTICS

[75] Inventors: Manuel Debono, Indianapolis; R. Michael Molloy, Danville; Ramakrishnan Nagarajan; Amelia A. Schabel, both of Indianapolis, all of Ind.

[73] Assignee: Eli Lilly and Company, Indianapolis, Ind.

[21] Appl. No.: 08/171,256

[22] Filed: Dec. 21, 1993

Related U.S. Application Data

[63] Continuation of application No. 07/996,373, Dec. 23, 1992, abandoned, which is a continuation of application No. 07/763,474, Sep. 20, 1991, abandoned, which is a continuation of application No. 07/630,376, Dec. 18, 1990, abandoned, which is a continuation of application No. 07/259,678, Oct. 19, 1988, abandoned.

[51] Int. Cl.⁷ ............................... C07K 7/50; C07K 9/00
[52] U.S. Cl. ........................................... 530/317; 530/322
[58] Field of Search ..................................... 530/317, 322

[56] References Cited

U.S. PATENT DOCUMENTS

| | | | |
|---|---|---|---|
| 4,029,769 | 6/1977 | Debono | 424/118 |
| 4,322,343 | 3/1982 | Debono | 260/112.5 R |
| 4,552,701 | 11/1985 | Nagarajan et al. | 260/112.5 R |
| 5,071,749 | 12/1991 | Kondo et al. | 530/317 |

FOREIGN PATENT DOCUMENTS

| | | |
|---|---|---|
| 0 231 111 | 8/1987 | European Pat. Off. . |
| 0265071 | 4/1988 | European Pat. Off. . |
| 0 273 727 | 7/1988 | European Pat. Off. . |

OTHER PUBLICATIONS

EPO published application 0265071 (Apr. 27, 1988), p. 1–5 of application.

*Primary Examiner*—Jeffrey E. Russel
*Attorney, Agent, or Firm*—Arlene K. Musser; Thomas G. Plant

[57] ABSTRACT

A82846-related glycopeptide compounds are prepared by treating an antibiotic selected from A82846 components A, B and C with trifluoroacetic acid to remove 1) the α-L-O-4-epi-vancosaminyl group attached to the disaccharide; 2) the (α-L-O-4-epi-vancosaminyl-β-O-glucosyl) disaccharide group or 3) both the disaccharide group and the α-L-O-4-epi-vancosaminyl group attached to the peptide core from these antibiotics. The compounds have antibacterial activity, especially against Gram-positive microorganisms.

14 Claims, 1 Drawing Sheet

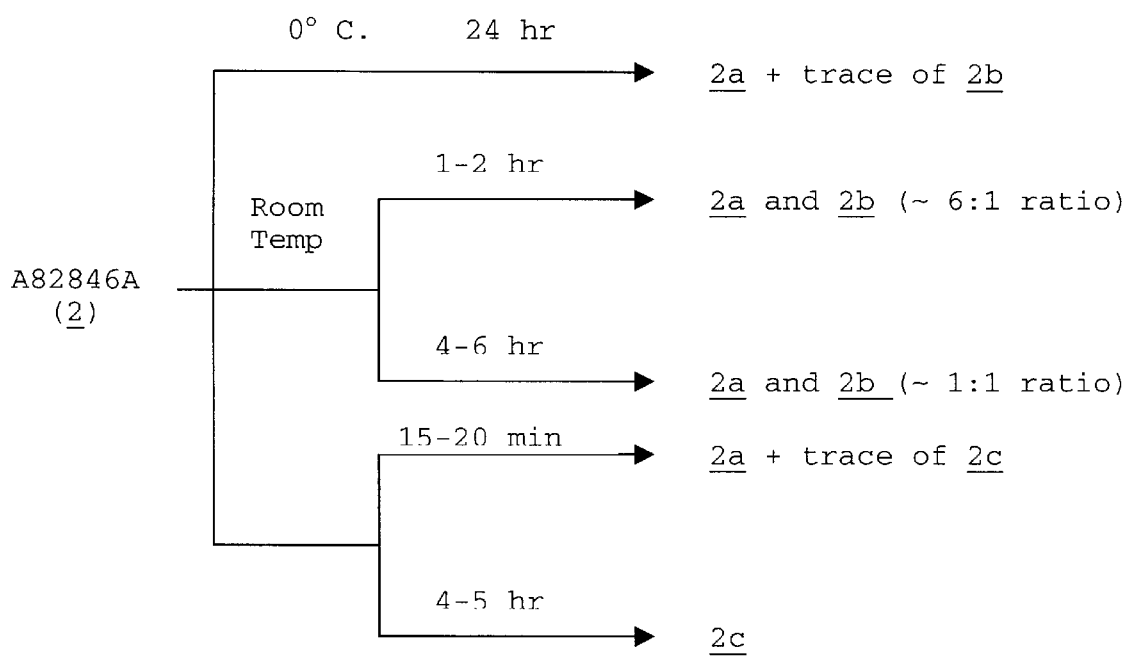

A-82846-TYPE GLYCOPEPTIDE ANTIBIOTICS

This application is a continuation of application Ser. No. 07/996,373, filed on Dec. 23, 1992, now abandoned, which is a continuation of application Ser. No. 07/763,474, filed on Sep. 20, 1991, now abandoned, which is a continuation of application Ser. No. 07/630,376, filed Dec. 18, 1990, now abandoned, which is a continuation of application Ser. No. 07/259,678, filed Oct. 19, 1988, now abandoned.

SUMMARY OF THE INVENTION

This invention relates to new glycopeptide compounds of formula 1:

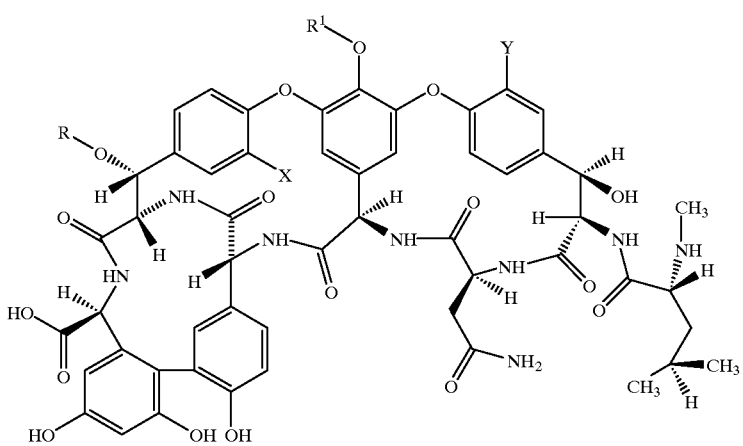

wherein R=H or

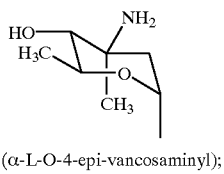

(α-L-O-4-epi-vancosaminyl);

$R^1$=H or

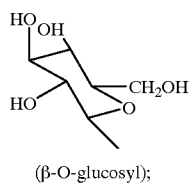

(β-O-glucosyl);

and
X and Y independently are H or Cl;
provided that: 1) when X is Cl, Y must also be Cl; and 2) when R and $R^1$ are both hydrogen, X and Y cannot both be Cl; or a salt thereof.

This invention also relates to methods for preparing the formula 1 compounds by treating an antibiotic selected from A82846 components A, B and C with trifluoroacetic acid (TFA) to remove 1) the α-L-O-4-epi-vancosaminyl group attached to the disaccharide; 2) the (α-L-O-4-epi-vancosaminyl-β-O-glucosyl) disaccharide group or 3) both the disaccharide group and the α-L-O-4-epi-vancosaminyl group attached to the peptide core from these antibiotics.

The formula 1 compounds retain excellent antibacterial activity, especially against Gram-positive microorganisms. Thus, this invention further provides useful compositions containing the formula 1 compounds and methods for treating infections using these compounds.

BRIEF DESCRIPTION OF THE DRAWING

The drawing is a schematic diagram that illustrates the effects of temperature and time on product formation when the starting material is A82846A.

DETAILED DESCRIPTION

This invention relates to new glycopeptide antibiotics, the formula 1 compounds, which are prepared from the A82846 antibiotics. The formula 1 compounds are also antibacterial agents and could be useful as intermediates to other antibiotics.

In the treatment of human diseases, there is an ongoing need for improved antibiotics. Vancomycin is a well known glycopeptide antibiotic currently used in human medicine. Vancomycin is especially useful for treating serious infections caused by methicillin-resistant staphylococci. There is a demand for new antibiotics which have the advantages of vancomycin but with improved antibacterial and pharmacokinetic properties.

Glycopeptide antibiotics contain a peptide core and one or more amino sugars and sometimes contain one or more neutral sugars. In order to obtain glycopeptide compounds like the formula 1 compounds, it is necessary to remove the various sugar moieties without damaging the complex peptide core during the procedure.

Previously, Nagarajan and Schabel were able to remove the sugar groups from certain vancomycin-type glycopeptides (See U.S. Pat. No. 4,552,701). Using another method, Debono obtained the pseudo-aglycones of actaplanin and antibiotic A35512 (See U.S. Pat. Nos. 4,322,343 and 4,029,769, respectively).

We have now succeeded in adapting the Nagarajan and Schabel procedures to remove the amino and neutral sugar groups from the A82846 antibiotics. The A82846 antibiotics have the structures shown in formulas 2–4 which follow:

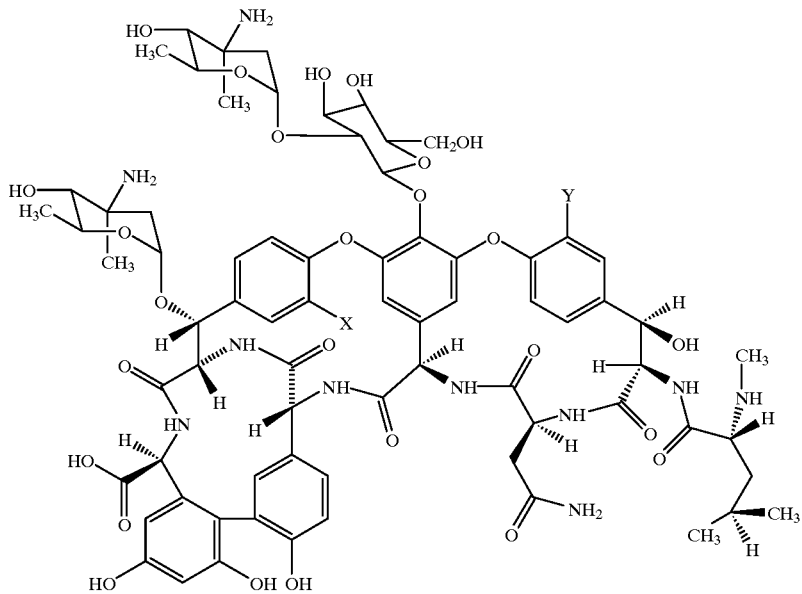

(2) A82846A: X = H  Y = Cl
(3) A82846B: X = Cl  Y = Cl
(4) A82846C: X = H  Y = H

Our methods selectively remove the A82846 sugars in the following order: 1) the (α-L-O -4-epi-vancosaminyl)-sugar from the disaccharide group; 2) the remaining (β-O-glucosyl)-sugar; and 3) the (α-L-O-4-epi-vancosaminyl)-sugar attached directly to the peptide core.

For convenience in discussions herein, the compounds of formula 1 formed when the first (α-L-O-4-epi-vancosaminyl)-sugar is removed [$R^1$=(β-O-glucosyl)] are called 1a or des-(α-L-O-4-epi-vancosaminyl)-A82846 compounds.

The formula 1 compounds formed when the remainder of the disaccharide group is removed ($R^1$=H) are called 1b compounds or pseudoaglycones.

The formula 1 compounds formed when all the sugar groups are removed (R and $R^1$=H) are called 1c compounds or aglycones.

The formula 1 compounds are listed in Table I.

TABLE I

| Formula 1 Compounds | | | | |
|---|---|---|---|---|
| Compound | X | Y | R | $R^1$ |
| 2a | H | Cl | epi-vancosaminyl | glucosyl |
| 2b | H | Cl | epi-vancosaminyl | H |
| 2c | H | Cl | H | H |
| 3a | Cl | Cl | epi-vancosaminyl | glucosyl |
| 3b | Cl | Cl | epi-vancosaminyl | H |
| 4a | H | H | epi-vancosaminyl | glucosyl |
| 4b | H | H | epi-vancosaminyl | H |
| 4c | H | H | H | H |

In one aspect, this invention relates to a process for preparing formula 1a, 1b and 1c compounds which comprises treating an A82846 antibiotic with TFA at a temperature of from about −10° C. to about 80° C. for a period of about 1 to 60 hours until the desired product is obtained.

At room temperature, shorter reaction periods (~1 to 2 hour) give 40% to 70% yields of 1a product and 50% to 20% yields of 1b products, whereas longer reaction periods (~24 hour) give lower yields of 1a product (10%→30%) and higher yields of 1b product (50–60%).

Higher temperatures favor formation of 1b and 1c compounds, whereas lower temperatures (e.g. 0° C.) favor formation of 1a compounds.

The schematic diagram in the drawings illustrates the effects of temperature and time on product formation when the starting material is A82846A.

The formula 1a compounds are useful intermediates for preparing formula 1b and 1c compounds; the formula 1b compounds are useful intermediates to the formula 1c compounds.

The formula 1 compounds each have a carboxyl group and one or more amino groups which can react to form various salts. The salt forms of formula 1 compounds are also part of this invention. The formula 1 salts are useful, for example, for separating and purifying the antibiotics.

The acid addition salts are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic and like acids.

Pharmaceutically acceptable acid addition salts are an especially preferred group of salts of this invention.

The formula 1 compounds have in vitro and in vivo activity against Gram-positive pathogenic bacteria. The minimal inhibitory concentrations (MIC's) at which the formula 1 compounds inhibit certain bacteria are given in Table II. The MIC's were determined by standard agar-dilution assays.

TABLE II

In Vitro Antibacterial Activity of Formula 1 Compounds[a]

| Test Organism | MIC (mcg/mL) | | | | |
|---|---|---|---|---|---|
| | 2a | 3a | 2b | 3b | 2c |
| Staphylococcus aureus X1.1 | 0.5 | 0.25 | 1 | 0.125 | 4 |
| Staphylococcus aureus V41[b] | 1 | 0.25 | 1 | 0.25 | 4 |
| Staphylococcus aureus X400[c] | 1 | 0.5 | 1 | 0.5 | 8 |
| Staphylococcus aureus S13E | 0.5 | 0.25 | 1 | 0.125 | 4 |
| Staphylococcus epidermidis 270 | 1 | 1 | 2 | 0.5 | 4 |
| Staphylococcus epidermidis 222 | 1 | 0.5 | 2 | 0.25 | 8 |
| Streptococcus pyogenes C203 | 0.5 | 0.25 | 1 | 0.25 | 4 |
| Streptococcus pneumoniae Park I | 1 | 0.25 | 1 | 0.25 | 4 |
| Streptococcus Group D X66 | 1 | 0.5 | 1 | 0.5 | 8 |
| Streptococcus Group D 2041 | 4 | 1 | 4 | 1 | 16 |
| Haemophilus influenzae C.L.[d] | —[f] | 64 | — | 32 | — |
| Haemophilus influenzae 76[e] | — | — | — | 64 | — |
| Escherichia coli EC14 | — | — | — | — | — |
| Klebsiella pneumoniae X26 | — | — | — | — | — |

[a]Compound numbers from Table I;
[b]Penicillin-resistant strain;
[c]Methicillin-resistant strain;
[d]Ampicillin-sensitive strain;
[e]Ampicillin-resistant strain;
[f]— = Not active at 128 mcg/mL, the highest level tested The formula 1 compounds have also shown in vivo antimicrobial activity against experimentally-induced infections in laboratory animals. When two doses of test compound were administered to mice experimentally infected with the test organism, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed for illustrative compounds are given in Table III.

TABLE III

In Vivo Activity of Formula 1 Compounds

| | $ED_{50}$ Value[a] | | |
|---|---|---|---|
| Compound[b] | Staphylococcus aureus | Streptococcus pyogenes | Streptococcus pneumoniae |
| 2a | 2.97 | 3.54 | 2.04 |
| 3a | 0.54 | 0.70 | 0.34 |
| 2b | 3.06 | 3.54 | 3.74 |
| 3b | 0.50 | 0.40 | 0.30 |

[a]mg/kg × 2; doses administered subcutaneously to mice 1 and 4 hours post-infection
[b]Compound numbers from Table I Pharmaceutical formulations of the formula 1 compounds are also part of this invention. Thus, the compound, preferably in the form of a pharmaceutically acceptable salt, can be formulated for oral or parenteral administration for the therapeutic or prophylactic treatment of bacterial infections.

For example, the compound can be admixed with conventional pharmaceutical carriers and excipients and used in the form of tablets, capsules, elixirs, suspensions, syrups, wafers and the like. The compositions comprising a formula 1 compound will contain from about 0.1 to about 90% by weight of the active compound, and more generally from about 10 to about 30%.

The compositions may contain common carriers and excipients, such as corn starch or gelatin, lactose, sucrose, microcrystalline cellulose, kaolin, mannitol, dicalcium phosphate, sodium chloride and alginic acid.

Disintegrators commonly used in the formulations of this invention include croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used.

It may be desirable to add a coloring agent to make the dosage form more esthetic in appearance or to help identify the product.

For intravenous (IV) use, a water soluble form of the antibiotic can be dissolved in one of the commonly used intravenous fluids and administered by infusion. Such fluids as, for example, physiological saline, RINGER'S solution or 5% dextrose solution can be used.

For intramuscular preparations, a sterile formulation of a suitable soluble salt form of the compound, for example the hydrochloride salt, can be dissolved and administered in a pharmaceutical diluent such as Water-for-Injection, physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of a suitable salt form of the antibiotic, for example, the hydrochloride salt, formulated in a diluent such as distilled or deionized water, is particularly useful.

Alternatively, the unit dosage form of the antibiotic can be a solution of the antibiotic, preferably in its salt form, in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

In a further aspect, this invention provides a method for treating infectious diseases, especially those caused by Gram-positive microorganisms, in animals. The animal may be either susceptible to, or infected with, the microorganism. The method comprises administering to the animal an amount of a formula 1 compound which is effective for this purpose. In general, an effective amount of a formula 1 compound is a dose between about 0.5 and about 100 mg/kg. A preferred dose is from about 1 to about 60 mg/kg of active compound. A typical daily dose for an adult human is from about 50 mg to about 1.0 g.

In practicing this method, the antibiotic can be administered in a single daily dose or in multiple doses per day. The treatment regime may require administration over extended periods of time, e.g., for several days or for from one to six weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via IV infusion. In this procedure a sterile formulation of a suitable soluble salt of the antibiotic is incorporated in a physiological fluid, such as 5% dextrose solution, and the resulting solution is infused slowly IV. Alternatively, the piggy-back method of IV infusion can also be used.

In order to illustrate more fully the operation of this invention, we provide the following examples:

EXAMPLE 1

Preparation of Compounds 2a and 2b

A82846A (500 mg, 0.32 mmol) was dissolved in TFA (100 mL) containing anisole (10 mL). The reaction mixture was stirred for 24 hr at room temperature under nitrogen. Volatile solvents were removed under vacuum to give a gray-tan residue. The residue was triturated with diethyl ether/chloroform (1:1, 50 mL×2). The solid material thus obtained (TFA salt) was dissolved in water (~50 mL), and the pH of this solution was adjusted to 6.2 with pyridine. The solution was filtered, and the filtrate was lyophilized to give 426 mg of an off-white powder. FAB—MS [M+1]: 1415, 1253, 1110. An HPLC scan showed two major peaks (in the amounts of ~23% and 43%).

This material was applied to a reverse-phase C-18 silica gel column (WATER'S PREP-PAK). Separation was accomplished by gradient elution of the column, starting with $H_2O$ containing 1% pyridinium acetate to 25% $CH_3CN/H_2O$ containing 1% pyridinium acetate (using a total of 8 L for the gradient, and then 2 L of the latter solvent to wash the column). Fractions of 250-mL were collected at a flow rate of 250-mL/min and were analyzed by TLC and HPLC.

Fractions containing compound 2a (#10–16) were combined and lyophilized to give 82 mg of compound 2a as a creme-colored solid. FAB—MS (P+1): 1414 (accurate mass calcd. for $C_{66}H_{77}N_9O_{24}Cl=1414.4770$; found: 1414.40).

Fractions containing compound 2b (#27–29) were also combined and lyophilized to give 128 mg of Compound 2b as a creme-colored powder. FAB—MS (P+1): 1252, 1109 (calculated for $C_{60}H_{67}N_9O_{19}Cl=1252.4242$; found: 1252.4240).

EXAMPLE 2

Preparation of Compounds 3a and 3b

A82846B (1 g) was dissolved in TFA (200 mL) containing anisole (10 mL). The reaction mixture was stirred at room temperature for about 2 hours under nitrogen.

The product was worked up as described in Example 1 to give 1.12 g of product. FAB—MS (M+1): 1448, 1305, 1286, 1252, 1142. HPLC demonstrated that this material contained two major peaks (in amounts of ~42% and 43%, respectively).

Preparative HPLC using the conditions described in Example 1, gave 283 mg of compound 3a. FAB—MS (P+1): 1448 (calculated for $C_{66}H_{76}N_9O_{24}Cl_2=1448.4380$; found: 1448.4375).

The preparative HPLC also yielded 270 mg of compound 3b. FAB—MS (P+1): 1286 (calculated for $C_{60}H_{66}N_9O_{19}Cl_2=1286.3852$; found: 1286.3879).

EXAMPLE 3

Prepration of Compounds 2b and 2c

A82846A (~490 mg) was dissolved in TFA (5 mL) and stirred in a 70° C. oil bath for two hours. The TFA was removed under vacuum; water was added to the residue, and the product was lyophilized to give 511 mg of crude product.

This material was divided into two batches (~250 mg each). Each batch was purified by preparative HPLC, using a WATER'S PREP-PAK DYNAMAX COLUMN (RAININ C18). Separation was accomplished by gradient elution of the column, with $H_2O$ containing from 10 to 20% $CH_3CN$ and 1% pyridinium acetate. Fractions were collected at a flow rate of 40 mL/min and analyzed by analytical HPLC.

Fractions containing compound 2b were combined and lyophilized to give 47 mg of compound 2b. FAB—MS (P+1): 1251.

Fractions containing compound 2c were also combined and lyophilized to give 47 mg of compound 2c. FAB—MS (P+1): 1108.

We claim:

1. A glycopeptide of the formula:

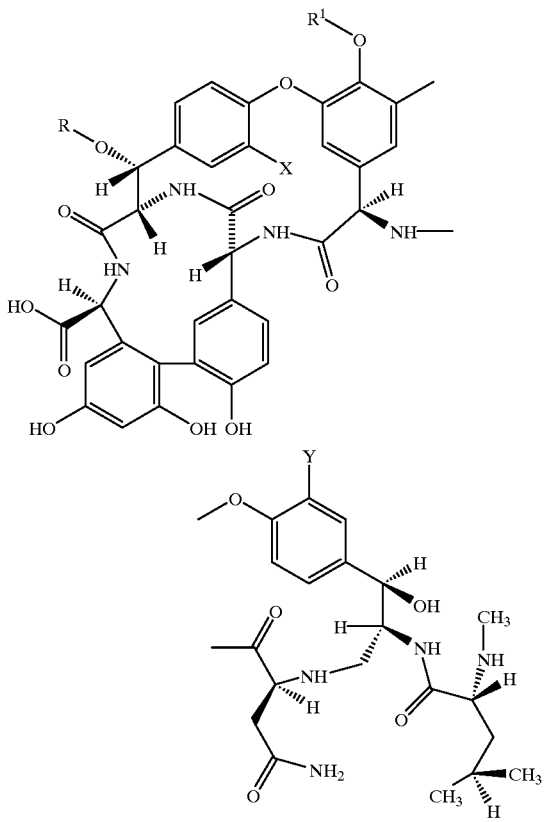

wherein
R=H or α-L-O-4-epi-vancosaminyl and $R^1$=H or β-O-glucosyl, provided that when R is H, $R^1$ must also be H; and
X and Y are independently H or Cl, provided that: 1) when X is Cl, Y must be Cl; 2) when R and $R^1$ are both hydrogen, X and Y cannot both be Cl; 3) when X and Y are both Cl, R must be α-L-O-4-epi-vancosaminyl; or a salt thereof.

2. A compound of claim 1 wherein X=H and Y=Cl.
3. The compound of claim 2 wherein R=H.
4. A compound of claim 2 wherein R=α-L-O-4-epi-vancosaminyl.
5. The compound of claim 4 wherein $R^1$=β-O-glucosyl.
6. The compound of claim 4 wherein $R^1$=H.
7. A compound of claim 1 wherein X and Y=Cl.
8. The compound of claim 7 wherein $R^1$=β-O-glucosyl.
9. The compound of claim 7 werein $R^1$=H.

10. A compound of claim 1 wherein X and Y=H.

11. The compound of claim 10 wherein R=H.

12. A compound of claim 10 wherein R=α-L-O-4-epi-vancosaminyl.

13. The compound of claim 12 wherein $R^1$=β-O-glucosyl.

14. The compound of claim 12 wherein $R^1$=H.

* * * * *